US010791750B2

(12) United States Patent (10) Patent No.: US 10,791,750 B2
Williams-Blair et al. (45) Date of Patent: Oct. 6, 2020

(54) CONFECTIONARY RESEMBLING JEWELS

(71) Applicants: Delores Williams-Blair, Mission Viejo, CA (US); Tatianna R. Blair, Mission Viejo, CA (US)

(72) Inventors: Delores Williams-Blair, Mission Viejo, CA (US); Tatianna R. Blair, Mission Viejo, CA (US)

(*) Notice: Subject to any disclaimer, the term of this patent is extended or adjusted under 35 U.S.C. 154(b) by 294 days.

(21) Appl. No.: 15/608,979

(22) Filed: May 30, 2017

(65) Prior Publication Data

US 2017/0339975 A1 Nov. 30, 2017

Related U.S. Application Data

(63) Continuation-in-part of application No. 14/529,108, filed on Oct. 30, 2014, now abandoned.

(51) Int. Cl.
| | |
|---|---|
| *A23G 3/50* | (2006.01) |
| *A23G 3/36* | (2006.01) |
| *A23G 3/48* | (2006.01) |
| *A61Q 11/00* | (2006.01) |
| *A61K 8/9706* | (2017.01) |
| *A61K 8/49* | (2006.01) |
| *A61K 8/67* | (2006.01) |
| *A61K 8/97* | (2017.01) |
| *A61K 8/02* | (2006.01) |

(52) U.S. Cl.
CPC .............. *A23G 3/50* (2013.01); *A23G 3/36* (2013.01); *A23G 3/362* (2013.01); *A23G 3/364* (2013.01); *A23G 3/368* (2013.01); *A23G 3/48* (2013.01); *A61K 8/0216* (2013.01); *A61K 8/4913* (2013.01); *A61K 8/676* (2013.01); *A61K 8/97* (2013.01); *A61K 8/9706* (2017.08); *A61Q 11/00* (2013.01)

(58) Field of Classification Search
None
See application file for complete search history.

(56) References Cited

U.S. PATENT DOCUMENTS

| | | | | |
|---|---|---|---|---|
| D437,671 | S * | 2/2001 | Fajerstein | ............... D1/106 |
| 6,455,096 | B1 * | 9/2002 | Katagiri | ........... A23G 3/04 |
| | | | | 426/660 |
| 7,051,894 | B2 * | 5/2006 | Barnes | ........ B65D 43/162 |
| | | | | 206/540 |
| 2011/0315567 | A1 * | 12/2011 | Boynton | ........ A45C 11/16 |
| | | | | 206/6.1 |
| 2016/0113987 | A1 * | 4/2016 | Choi | .............. A23G 3/54 |
| | | | | 424/439 |

FOREIGN PATENT DOCUMENTS

| | | | |
|---|---|---|---|
| WO | WO 2006127599 | * | 11/2006 |
| WO | WO 2011/117635 | * | 9/2011 |

* cited by examiner

*Primary Examiner* — Tigabu Kassa
(74) *Attorney, Agent, or Firm* — Roy A. Ekstrand

(57) ABSTRACT

Confectionary shaped and configured to resemble jewels are provided with various color tints and flavor enhancements. The confectionary are further enhanced by fabrication which includes formulations effective in improving the user's breath and oral hygiene. Novel packaging for supporting and presenting the confectionary resembling jewels are also provided. A dispensing wand receives and supports a plurality of confectionary resembling jewels and is operable to sequentially dispense the confectionary resembling jewels.

4 Claims, 7 Drawing Sheets

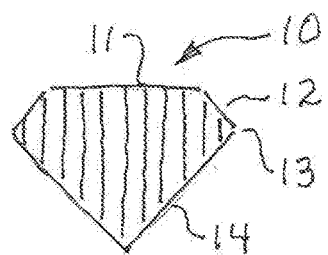 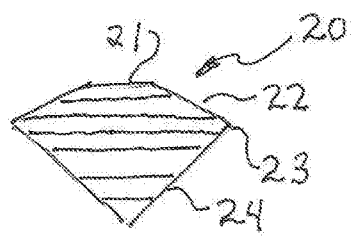 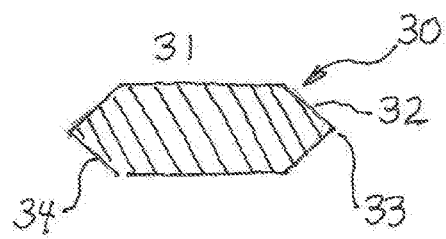
Fig 2A   Fig 2B   Fig 2C
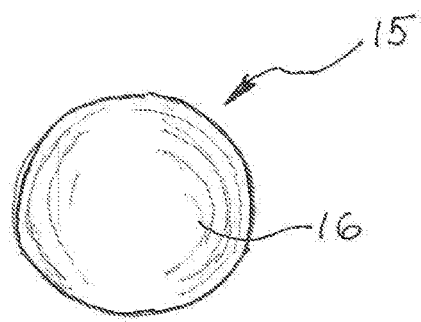 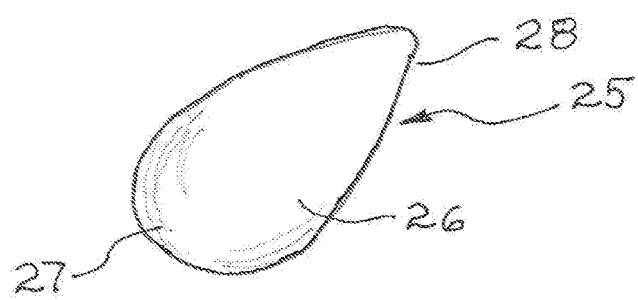
Fig 3A   Fig 3B

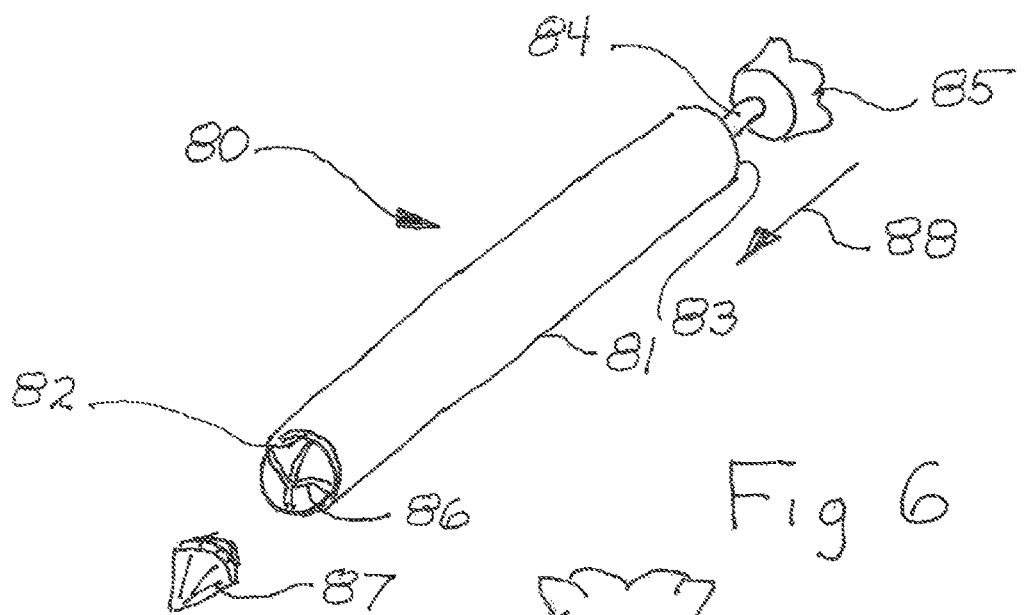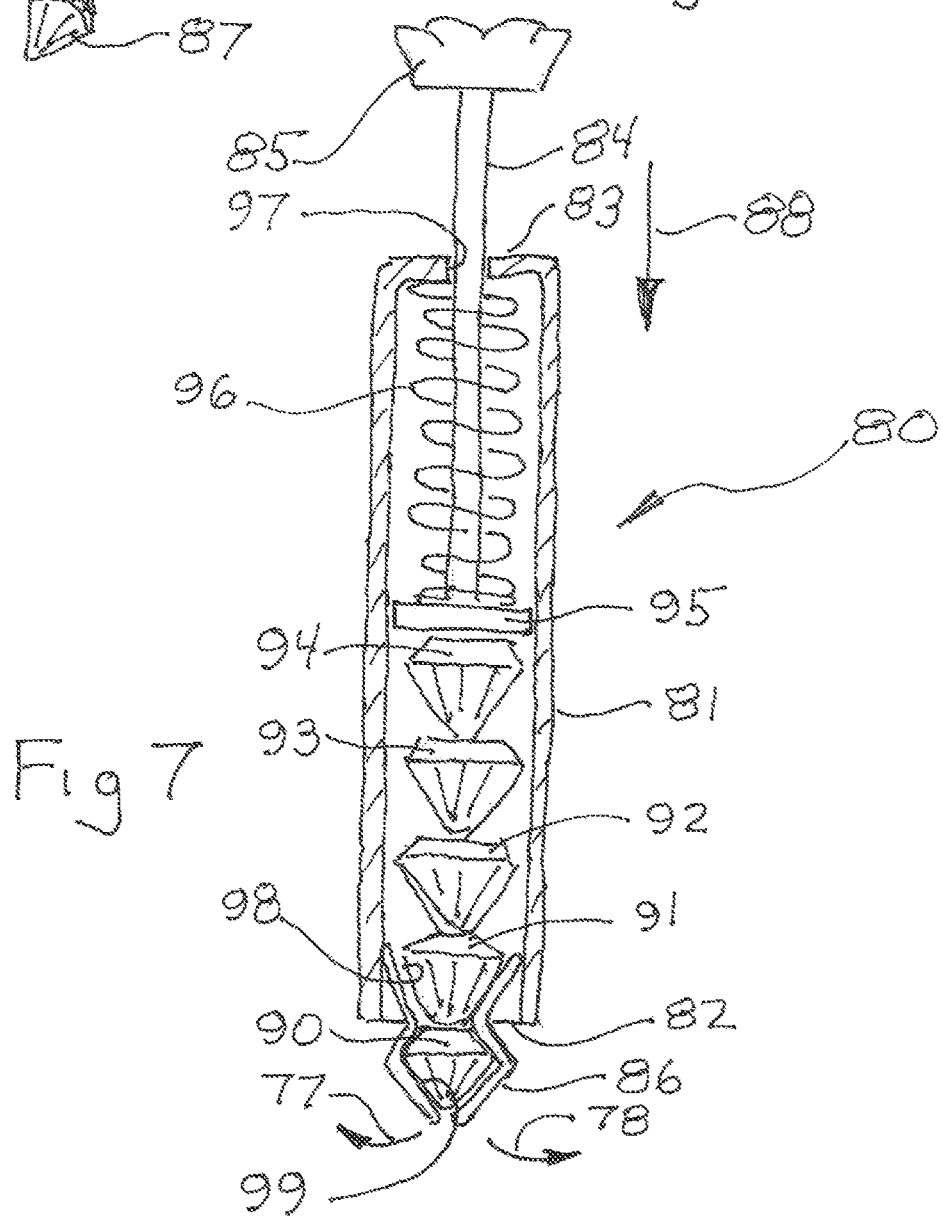

CONFECTIONARY RESEMBLING JEWELS

CROSS-REFERENCE TO RELATED APPLICATION

This application is a Continuation-in-Part of co-pending patent application Ser. No. 14/529,108 entitled CONFECTIONARY RESEMBLING JEWELS, filed Oct. 30, 2014 in the name of Delores Williams-Blair, et al, the disclosure of which is incorporated herein by reference.

FIELD OF THE INVENTION

This invention relates generally to confectionary such as candy or other items and relates more particularly to confectionary items known generally
in the art as "breath mints". This invention relates further to various amusement and novelty aspects intended to enhance the appeal and attractiveness of such confectionary items.

BACKGROUND OF THE INVENTION

Confectionary items, more commonly and generally known as "candy", have been provided by practitioners in the food arts for many years. From the earliest days of recorded history most societies enjoyed some type of sweet treat or confectionary item. As time passed, these confectionary items began to be provided in the form of candy having a virtually endless variety of flavors, appearances, and shapes. As practitioners in the confectionary arts endeavored to enhance the appeal and attractiveness of confectionary products, one area of activity tended to focus upon the appearance of the confectionary or candy items. Thus, candy has been provided which is attractive in color and sparkling in appearance with the intent to attract the consumer. Additionally, candy has been provided in which practitioners have wrapped the candy items in a variety of highly colorful wrappings or packaging.

In a related art, practitioners in the confectionary arts have also endeavored to provide candy which produces an additional result beyond simply tasting good. One example of such additional results in confectionaries and candies has been the provision of so-called "breath mints". Breath mints derive their popular name from the combination of candies directed toward enhancing or improving the consumers breath and oral hygiene. Additionally, the candies assumed the mint name due largely to the tendency for breath mint formulators to include a flavoring and fragrance item which is best described as a mint flavor or fragrance. While breath mints may have been originally created with the primary intent of improving the users breath fragrance and reducing breath odor, in recent years formulators have also directed their efforts toward more serious objectives such as improving the users oral hygiene by attempting to reduce or attack various potentially injurious enzymes and the like often found within the user's mouth.

As practitioners the confectionary arts have conducted the above-described types of activities directed toward the improving the attractiveness and appeal of candy products, a number of types of candy have been provided which define shapes resembling jewels such as diamonds, emeralds and the like. For example, U.S. Pat. D437,671 issued to Fajerstein sets forth a DIAMOND-SHAPED CANDY in which candy items have faceted shapes corresponding to a wide variety of well-known and established diamond cuts are presented.

U.S. Pat. D500,907 issued to Kraus sets forth a FOOD BLEND PRODUCT having various food items assuming shapes such as polygons, stars or the like.

U.S. Pat. D649,738 issued to Hollmann sets forth CONFECTION showing a candy item having a polygon shape defining a faceted upper face.

U.S. Pat. Des. 287,780 issued to Farber sets forth CANDY showing a candy item having a silhouette suggesting a diamond or similar gem stone.

U.S. Pat. Des. 242,646 issued to Shorin et al sets forth a COMBINED CANDY AND RING having a finger mounting ring supporting a generally planar base on the crown thereof. A gem-shaped candy item is supported upon the base and extends upwardly from the base.

U.S. Pat. Des. 242,645 issued to Shorin et al sets forth RING HAVING A MATRIX FOR CANDY which includes a ring supporting a planar base on the ring crown. A small candy item resembling a gem is supported on the base.

In a related art, U.S. Pat. Des. 275,615 issued to Eoga sets forth a PHARMACEUTICAL TABLET having a generally rectangular shape and defining a plurality of faceted surfaces on the upper surface and lower surface of the tablet.

French patent 2,603,167 issued to Amegninou sets forth a plurality of pendant designs incorporating confectionary elements.

Additional examples of jewelry shaped candy and confectionary items are found in Japanese publication JP2010200612, JP2006238890, and French publication FR260,3167A While the foregoing described prior art devices and products have to some extent improved the art and in some instance enjoyed commercial success, there remains none the less a continuing and unresolved need in the art for ever more improved, interesting, amusing and effective confectionary products.

SUMMARY OF THE INVENTION

Accordingly, it is a general object of the present invention to provide an improved confectionary product. It is a more particular object of the present invention to provide an improved confectionary product which, in addition to providing attractive taste, also performs beneficial therapies for the consumer. It is still more particular object of the present invention to provide an improved confectionary product which is supplied in an attractive and appealing packaging.

In accordance with the present invention, there is provided a confectionary or candy product formed of a hard transparent material which defines a color tint and faceted appearance suggestive of a jewel. The jewel candy thus provided utilizes a combination of shape, color and flavor in a coordinated arrangement to further enhance the jewel-like perception. The candy further provides a breath mint formulation which enhances the mouth hygiene of the user. Additionally, the inventive candy jewel-like product is provided with an attractive package reflecting a royal or treasure theme.

In another aspect, the present invention provides an attachment device which receives and supports a plurality of gem-shaped candies and which facilitates transferring and dispensing jewel-like candies.

In accordance with the present invention, there is provided a confectionary comprising: a jewel-shaped candy defining a color tint and flavor; a breath-enhancing substance added to the jewel-shaped candy; and a package receiving and displaying the jewel-shaped candy, the jewel-shaped candy formulated to include: a Xylitol base ingredient, a fruit sugar, a saliva producing ingredient, and a flavor ingredient.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

FIGS. 2A, 2B and 2C set forth section views of the present invention confectionary jewels shown in FIGS. 1A, 1B and 1C respectively;

FIG. 3A sets forth a perspective view of an alternate embodiment of the present invention confectionary defining a generally spherical shape and a pearl-like appearance;

FIG. 3B sets forth a perspective view of a still further alternate embodiment of the present invention confectionary providing a tear-drop shaped pearl resembling confectionary;

FIG. 6 sets forth a front view of a dispensing wand utilized in dispensing confectionary items constructed in accordance with the present invention;

FIG. 7 sets forth a section view of the dispensing wand shown in FIG. 6;

DESCRIPTION OF THE PREFERRED EMBODIMENTS OF THE INVENTION

FIGS. 1A through 1F set forth illustrative shapes of candy defining general appearances which correspond to the various cuts or shapes of jewels presently available in the market. It will be apparent to those skilled in the art that the shapes and cuts selected for resemblance in FIGS. 1A through 1F is merely provided for purposes of illustration and not limitation. Thus, it will be understood that the present invention may be fabricated in virtually any jewel shape without departing from the spirit and scope of the present invention. In addition, and in accordance with an important aspect of the present invention, jewel shapes 1A through 1F will be understood to be fabricated to present a selected color and flavor. For example, candy 10 shown in FIG. 1A may be fabricated using a clear transparent candy formula to resemble a clear transparent diamond or maybe, tinted red to represent a ruby. Similarly, candy 30 shown in FIG. 1C may be fabricated and colored to present a transparent green color to represent an emerald stone. Similarly, candy 40 shown in FIG. 1D may be fabricated to present a light violet color indicative of an amethyst stone.

By way of further illustration, and in further accordance with the present invention, the illustrative candies shown in FIGS. 1A through 1F are provided in the manner described below with a selected flavor combination which in the preferred fabrication of the invention is selected in correspondence to the color of the jewel. As a result, the present invention candies provide a color to flavor correspondence. Thus, for example, a cherry flavor may be utilized to flavor candies having a red color while a mint flavor may be selected for candies having a green color. Continuing this illustration, a transparent candy may be provided with a basic sweet flavor while a blue colored candy may be provided with a "cool mint" flavor.

Figure 1A:
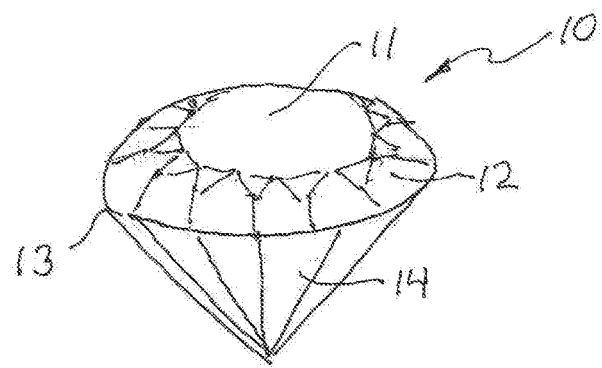
FIGS. 1A through 1F set forth perspective views of alternate shapes provided for the present invention confectionary resembling jewels.

More specifically, FIG. 1A sets forth a candy generally referenced by numeral 10 which is configured to illustrate a round diamond shape. Thus, candy 10 includes a top facet 11 and a plurality of angled facets 12, a generally circular edge 13 and a generally conical faceted base 14.

Figure 1B:
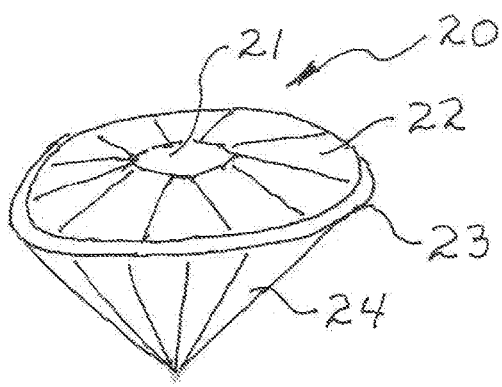

FIG. 1B sets forth a candy generally referenced by numeral 20 which defines an oval cut gem shape formed by a top facet 21 and a plurality of angled side facets 22. An oval edge 23 encircles facets 22 and a faceted tapered base 24 completes candy 20.

Figure 1C:
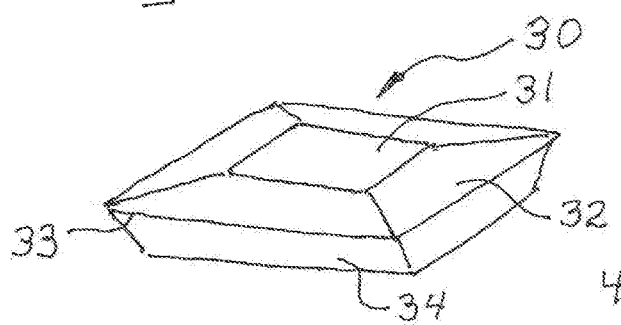

FIG. 1C sets forth a further alternate embodiment of the present invention candy generally referenced by numeral 30. Candy 30 is shaped to resemble an emerald cut stone and thus includes a top face 31, a plurality of side facets 32, a generally rectangular edge 33 and a tapered base 34.

Figure 1D:
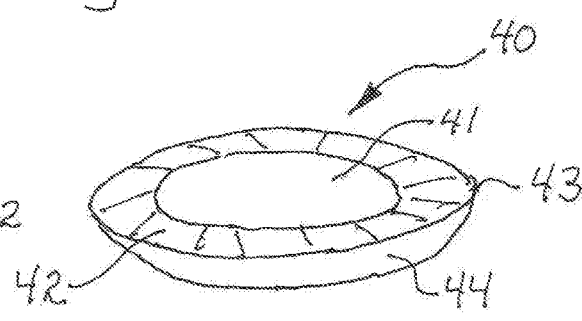

FIG. 1D sets forth a still further alternate embodiment of the present invention candy generally referenced by numeral 40. Candy 40 is shaped to resemble a marquise-shaped jewel and thus defines a top facet 41 and side facets 43 together with a generally oval, pointed edge 42 and a tapered base 44.

Figure 1E:
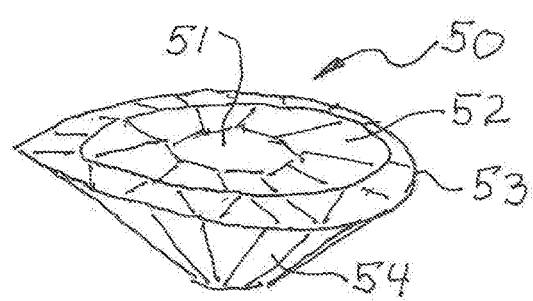

FIG. 1E sets forth a still further alternate embodiment of the present invention candy generally referenced by numeral 50. Candy 50 is shaped to resemble a jewel having a pear-shape having a top facet 51, side facets 53 and a teardrop-shaped edge 52. Candy 50 further includes a tapered base 54.

Figure 1F:
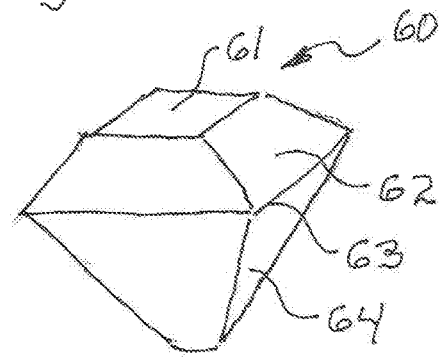

FIG. 1F sets forth a still further alternate embodiment of the present invention candy generally referenced by numeral 60. Candy 60 is shaped to provide resemblance to a "table" gem shape and thus includes a top facet 61 together with side facets 63 and a square edge 62. Candy 60 further includes a tapered base 64.

FIGS. 2A, 2B and 2C set forth section views of confectionary jewels 10, 20 and 30 shown in FIGS. 1A, 1B and 1C above. Of importance to notes in FIGS. 2A through 2C is the different colors for which each section viewed is lined. Thus, candy jewel 10 shown in FIG. 2A which is a section view of jewel 10 shown in FIG. 1A lined to indicated the color red. This in the world of gems and precious stones is typically understood to represent a ruby gem stone. It will be understood of course that candy 10 could be colored utilizing virtually any color tint to represent other stones. Similarly, FIG. 2B sets forth candy 10 in section view showing color indication for the color blue. This represents perhaps a blue diamond or other blue colored gem stone. Similarly, candy 30 is shown in FIG. 2C lined to indicate a green color which in the world of gem stones is typically understood to defines an emerald stone. Once again, it will be understood that each of the candies shown in FIGS. 2A through 2C may be tinted with other colors as desired. In addition to color tinting and in accordance with an important aspect of the present invention, the present invention candies resembling jewels are preferably flavored to provide a breath mint character and flavor. In further addition, each of the candies provided in accordance with the present invention will also preferably utilize a flavoring which is coordinated to or related to the flavor typically suggested by its color. Thus, for example, candy 10 which is tinted red may in addition to having breath mint flavoring also utilize a flavoring such as "cherry" indicative of or related to the color red. Similarly, candy 20 which is tinted blue may in addition to breath mint flavoring also bear flavoring such as cool mint to correspond to the suggested or coordinated flavoring associated with the color blue. By way of further example, candy 30 which is tinted green may in addition to breath mint flavoring also include a flavoring component coordinated to or related to the color green such as "spearmint". It will be apparent to those skilled in the art that a variety of flavorings and tinting may be utilized in multiple combinations in accordance with the present invention. Thus, the examples set forth above should not be considered by way of limitation but rather simply illustrative of the vast variety of flavoring and tinting combinations which confectioners can achieve.

While the foregoing illustrations of the present invention candy set forth in FIGS. 1A through 1F utilize a hard transparent and in most instances color tinted candy, FIGS. 3A and 3B set forth further alternate embodiments of the present invention candy in which the candy is fabricated to generally resemble a pearl. Thus, FIG. 3A sets forth a pearl-like candy 15 defining a spherical surface 16 while FIG. 3B sets forth a candy 25 defining a teardrop-shaped body 27 having a pointed end 28 and a teardrop surface 26. Both candy 15 and candy 25 are formed of similar materials which unlike the above-described embodiments of the invention are formulated to present a pearl-like appearance. Once again, it will be apparent to those skilled in the art that the flavoring selected for candies 15 and 25 is chosen to be selective or representative of the appearance suggestion given by a pearl gem. For example, a somewhat creamy vanilla flavor may be appropriate for pearl-like candies 15 and 25.

In accordance with an important aspect of the present invention, the inventive candies are preferably formulated to provide a breath mint therapeutic benefit. Accordingly, and as is mentioned above, the present invention confectionary resembling jewels referred to herein as simply "candy" is preferably crafted as a transparent hardened isomalt in a variety of breath freshening and therapeutic breath enhancing flavors. As is also mentioned above, the present invention confectionary are resembling jewels are produced in an assortment of jewel shapes, such as round diamond cut, oval cut sapphire, ascher cushion cut ruby, basic rectangular emerald, and white pearls of differing shapes. As is also mentioned above, the various jewel resembling candies fabricated in accordance with the present invention will be variously colored and tinted with the object of producing vibrant color and glimmer appearance attained by utilizing edible sparkle dust all with the objective of providing the closest appearance to authentic gems. In addition, the formula utilized in fabricating the present invention confectionary resembling jewels employs ingredients that in addition to be tasty are also affective at helping to produce oxygen and neutralized acid in the mouth of the user in a mimicking of human saliva. This in turn tends to rebalance the oral ecology of the user's mouth.

In further accordance with the therapeutic aspects of the present invention and the objective to avoid increasing the sugar intake of the user, the preferred fabrication of the present invention confectionary resembling jewels utilizing formulae which are sugar-free and equally free of artificial sweeteners such as saccharin or aspartame which have been found to increase odor causing bacteria once dissolved and which are also known to produce a bitter aftertaste residue in the mouth of the user. As a healthier alternative, the present invention confectionary resembling jewels utilize a base ingredient known in the art as "Xylitol" which is a natural herb and sweetening agent originally found in beech trees indigenous to Austria. The advantage of utilizing Xylitol as a base ingredient includes the imparting of a very pleasing sweetness to the user. In addition, the use of Xylitol also releases a microbial power within the user's mouth that breaks down the bacteria known to cause tooth decay and decreases the build-up of anaerobic sulfur compounds upon the user's tongue and throat surfaces.

Accordingly, in the formulation of the present invention confectionary resembling jewels, Table 1 sets forth a plurality of odor neutralizing base ingredients as follows:

TABLE 1

Sorbitol (sweetener made of fruit sugar, specifically apples and peaches)
Xylitol
Sodium bicarbonate
Dicalcium phosphate
Citric acid
Fumaric acid
Calcium stearate
Calcium peroxide
Zinc glutonate
Menthol
Oil of Clove
Natural anise oil
Licorice powder Additionally, the formulation of the present invention confectionary resembling jewels also includes a plurality of saliva producing or enhancing ingredients set forth below in Table 2 as follow.

TABLE 2

Sorbitol
Xylitol
Maltodextrin
Magnesium stearate (from plant sources)
Zinc gluconate
Rebiana (from Stevia)

To provide the desired flavor and taste for the present invention confectionary resembling jewels, a plurality of flavoring options are selected from the ingredients set forth below in Table 3 as follows:

TABLE 3

Peppermint oil
Spearmint, Wintergreen, Menthol
Fennel
Anise
Cloves
Cardamom
*Chrysanthemum*
Dill
Fenugreek TABLE 3-continued Rosemary
Tarragon
*Eucalyptus*
Coriander
Cinnamon
Sage
Chlorophyll (natural deodorant) rich herbs such as parsley, spirulina, chlorella and wheat grass
*Aloe vera*, Green Tea (Catechin - antioxidant),
Vitamin C and natural probiotics
Hawthorn berry extract (astringent that repairs gums)
*Echinacea* (bactericidal), thyme and ginger The above described formulations of the present invention confectionary items provide substantial health and oral hygiene benefits not realized in prior art confectionary products. Thus, the inventive confectionary items are active to neutralize the various sulfur compounds which would otherwise be present upon the user's tongue, inner cheek lining and upper throat. Additionally, the inventive confectionary items perform deodorization of the user's mouth and throat rather than simply covering odor as most so-called "breathe mints" do. An important benefit provided by the above formulations of the present invention confectionary items is found in the increased saliva production which is stimulated. The inventive formulations rely upon and encourage natural bacteria dissolving action rather than using harsh artificial chemical agents.

Figure 4:
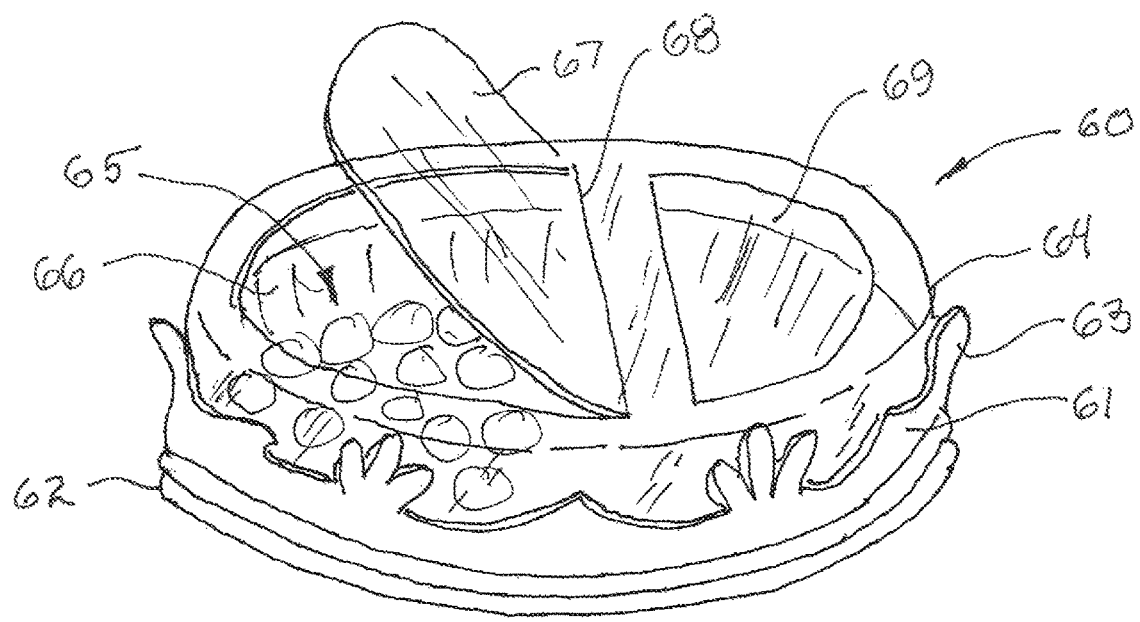
FIG. 4 sets forth a perspective view of a confectionary package utilized in supporting the present invention confectionary generally resembling a crown.

FIG. 4 sets forth a perspective view of a package utilized in packaging and presenting the present invention confectionary resembling jewels generally referenced by numeral 60. Package 60 is configured to replicate a "crown" of the type born by monarchs throughout the world. The intention of package 60 is to suggest a crown or royalty further enhancing the presentation of the present invention confectionary resembling jewels. Thus, package 60 formed to represent a crown includes a base 62 and an upwardly extending decorative wall 61. Wall 61 defines a plurality of outwardly curving flutes 63 forming a receptacle sidewall within which an enclosure 64 is joined to the interior of base 62. Enclosure 64 is sealed to the interior of base 62 to provide an air-tight packaging receptacle for preserving the present invention confectionary items illustrated by confectionary items 65. Enclosure 64 is preferably formed of a clear or transparent material and is lined with a soft fabric liner 66. In the preferred embodiment of the invention, liner 66 is formed of a velvet fabric intended to be consistent with the "royalty" theme of the invention. Enclosure 64 further defines a lid 67 which is pivotally secured to enclosure 64 by a "living hinge" 68. Enclosure 64 also includes a second lid 69. Lids 67 and 69 form an air-tight closure of enclosure 64 when snapped closed. Either of lids 67 or 69 may be opened to provide access to the plurality of confectionary items 65, constructed in accordance with the present invention, that are deposited within enclosure 64. In the preferred fabrication of the present invention, package 60 is aesthetically enhanced to represent a golden crown or the like.

Figure 5:
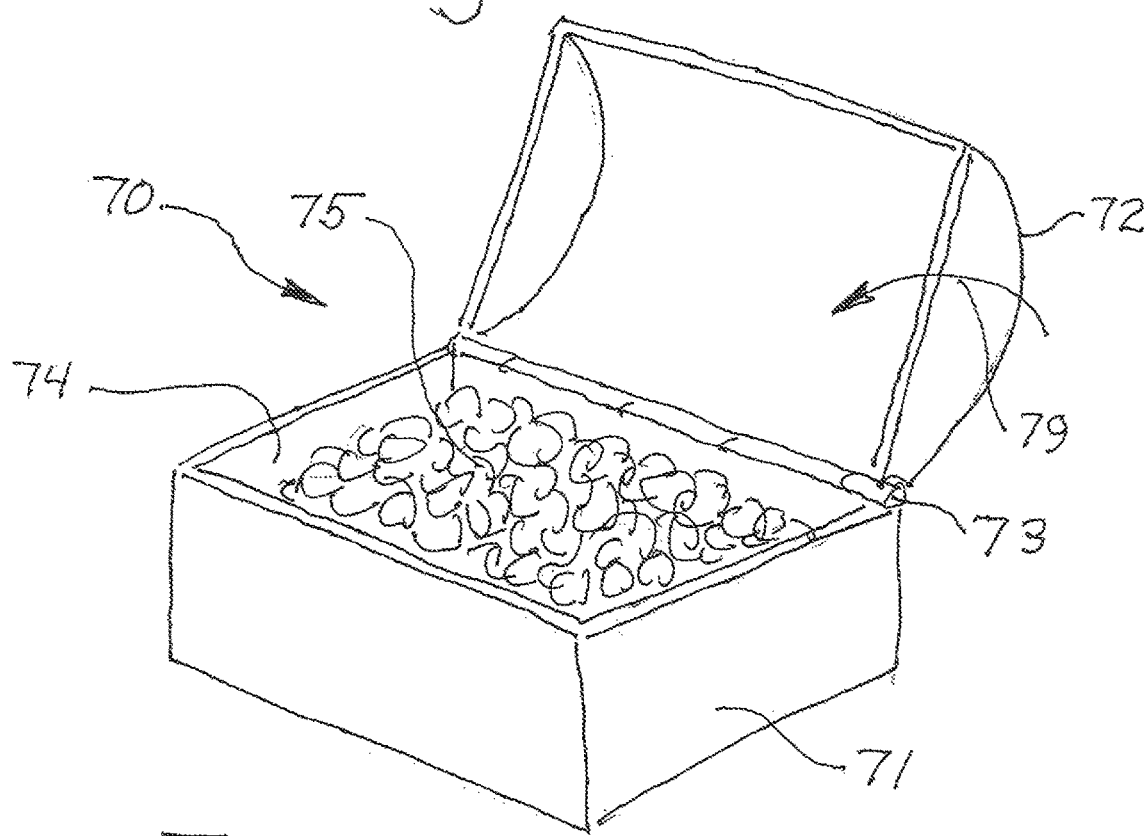
FIG. 5 sets forth a perspective view of an alternate embodiment package for use in supporting the present invention confectionary generally resembling a treasure chest.

FIG. 5 sets forth a perspective view of an alternate package generally referenced by numeral 70 which may also be utilized in packaging and presenting the present invention confectionary resembling jewels. Package 70 is fabricated to resemble a "treasure chest" suggestive of the treasure chests utilized in various pirate stories or fairy tales throughout history. Thus, package 70 includes a generally rectangular open top base 71 having an interior cavity 74 formed therein. Package 70 further includes a generally semi-cylindrical lid 72 sized to be received upon the upper edge of base 71. Lid 72 is pivotally secured to the upper edge by base 71 by a conventional hinge 73.

It will be apparent to those skilled in the art that package 70 is shown having lid 72 in its open position exposing interior 74. It will be equally apparent to those skilled in the art that lid 72 pivots about hinge 73 in the direction indicated by arrow 70 to close interior 74 of package 70. Interior 74 supports a quantity of confectionary resembling jewels constructed in accordance with the present invention and generally referenced by numeral 75. In the preferred fabrication of the present invention, confectionary 75 are randomly distributed within interior 74 to present the image of a treasure chest filled with valuable jewels.

FIG. 6 sets forth a perspective view of a candy supporting and dispensing wand generally referenced by numeral 80. Wand 80 includes an elongated generally tubular housing 81 having a closed upper end 83 and an open lower end 82. Open end 82 further supports a plurality of resilient flexible tines 86 shaped in the manner shown in FIG. 7 to receive and support a jewel resembling confectionary such as confectionary 87. Wand 80 further includes a plunger 84 which in the manner better seen in FIG. 7 passes through closed end 83 and is coupled to a plunger 95 also best seen in FIG. 7.

FIG. 7 sets forth a section view of wand 80 which as described above includes a generally elongated tubular housing 81 defining an interior wall 89, an open end 82 and a closed end 83. As is also described above, wand 80 includes a plunger rod 84 having a knob 85 at the upper end thereof. Plunger rod 84 extends downwardly through aperture 97 formed in closed end 83 and supports plunger 95 at its lower end. A spring 96 encircles plunger rod 84 and is captivated within tubular housing 81 by closed end 83 and plunger 95. Spring 96 is an expansive spring producing a spring force which urges plunger 95 downwardly in the direction indicated by arrow 88.

Wand 80 further includes a plurality of spring tines 86 which are secured to interior wall 89 of tubular housing 81. Tines 86 are shaped to provide a receiving position 98 within open end 82 and an exposed position 99 beneath open end 82. For purposes of illustration, a plurality of confectionary jewels 90, 91, 92, 93 and 94 are shown received within wand 80. Confectionary 90 is shown supported by tines 86 at exposed position 99 while confectionary 91 is shown supported by tines 86 at receiving position 98. Confectionaries 92 through 94 are serially stacked within wand 80 and are maintained in position by plunger 95 and the force of spring 96.

In operation, the user dispenses confectionary 90 from tines 86 by pressing knob 85 downwardly in the direction indicated by arrow 88. The force of plunger 95 is communicated through confectionaries 92, 93 and 94 to confectionary 91 forcing it against the inclined portions of tines 86. This force causes tines 86 to be pivoted outwardly in the direction indicated by arrows 77 and 78. This in turn releases confectionary 90 and replaces it with confectionary 91. In this manner, confectionary 90 has been dispensed from wand 80. Thereafter, confectionary 91 may be dispensed from position 99 in the same manner by pressing downwardly by know 85 in the direction indicated by arrow 88.

Figure 8:
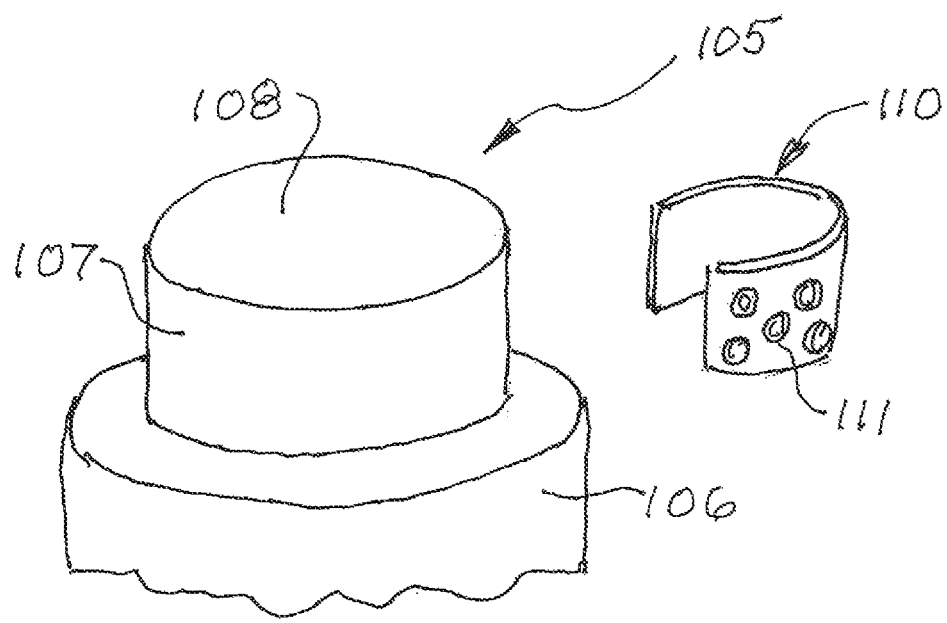
FIG. 8 sets forth a perspective view of a cake having an alternative jewel-like confectionary attachment apparatus.

FIG. 8 sets forth a perspective view of a conventional cake generally referenced by numeral 105 having a base 106, a raised generally cylindrical side 107 and a top surface 108. Once again, it will be understood that cake 105 is fabricated entirely in accordance with conventional fabrication techniques. In accordance with such conventional fabrication techniques, it will be understood that base 106, side 107 and top surface 108 are covered with a layer of soft frosting. In accordance with the present invention, a generally planar wrap 110 is formed in a semi-cylindrical shape and is utilized in supporting a plurality of confectionary resembling jewels constructed in accordance with the present invention and generally referenced by numeral 111. Wrap 110 may be fabricated utilizing virtually any material sufficient in strength to maintain its shape and support confectionaries 111. Wrap 110 is then placed upon side 107 to decorate and enhance the appearance of cake 105.

Figure 9:
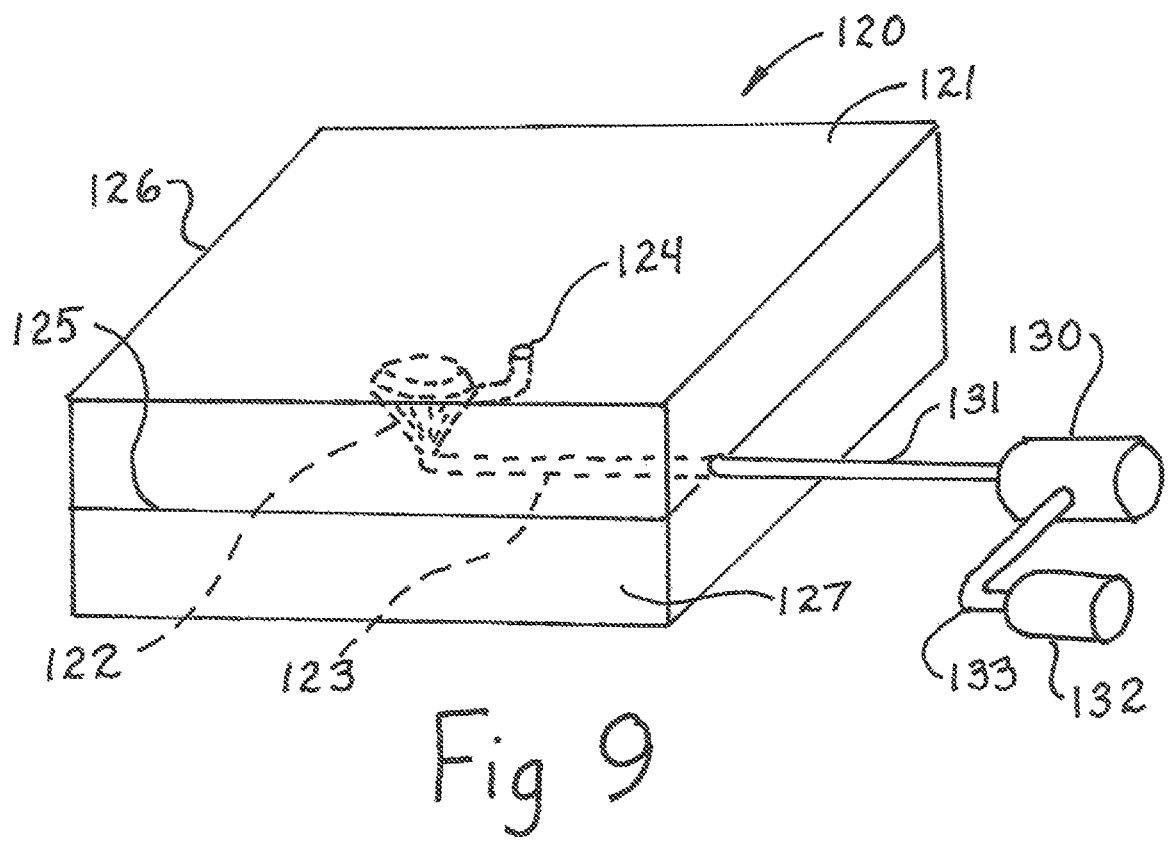
FIG. 9 sets forth a perspective view of an illustrative mold used in fabricating the present invention confectionary resembling a jewel.

FIG. 9 sets forth a perspective view of an illustrative mold which may be used in fabricating a confectionary jewel constructed in accordance with the present invention. It will be apparent to those skilled in the art that the mold shown in FIG. 9 is merely for purposes of illustration in that the mold is highly simplified and shows a single confectionary being formed. As is well known, conventional injection molding molds typically utilize a plurality of mold cavities to produce a plurality of molded parts during each cycle. In the illustration of FIG. 9, a single mold cavity is shown for simplification.

Thus, FIG. 9 shows an injection mold generally referenced by numeral 120 having a mold body 121 typically formed of a metal, a ceramic or other suitable material. Mold body 121 is formed of an upper half 126 and a lower half 127 which meet at a parting line 125. Thus, mold body 120 is able to be joined at parting line 125 or separated into halves 126 and 127. Within the interior of mold body 120, a mold cavity 122 is formed. Mold cavity 122 is shaped to define the outside surfaces of the three dimensional part that is formed in the molding process. In this instance, mold cavity 122 is formed in the three dimensional shape of a conventional round cut diamond. Mold body 121 also defines an input passage 123 which is in communication with mold cavity 122. A conventional injection molder 130 is coupled to input 122 by an input supply 131. An additive supply 132 is coupled to injection molder 130 by an additive supply line 133. Mold body 120 also defines a riser 124 in communication with mold cavity 122.

In operation, mold halves 126 and 127 are joined along parting line 125 to form a closed mold. Thereafter, injection molder 130 compresses a confectionary material formulated in the above manner to produce a confectionary liquid Concurrently, additive supply 132 adds a preselected mixture of color and flavor additives which are also combined with the liquid confectionary. The resulting mix of confectionary and additives is injected through supply 131 and input 123 to fill mold cavity 122. In accordance with conventional molding techniques, mold cavity 122 is "overfilled causing some material to fill riser 124. This ensures that mold cavity 122 is completely filled with material and prevents the formation of air bubbles within mold cavity 122. In accordance with an important aspect of the present invention, the flow and content of additives added to the liquid confectionary may result in a complete mix, tinting the mold confectionary or may be partially mixed to produce a molded confectionary with color variations, as desired. Once the liquid confectionary has cooled, mold body 121 is opened by separating halves 126 and 127. The molded confectionary is removed from mold cavity 122 and the tailings formed in riser 124 and supply input 125 are removed.

Figure 10:
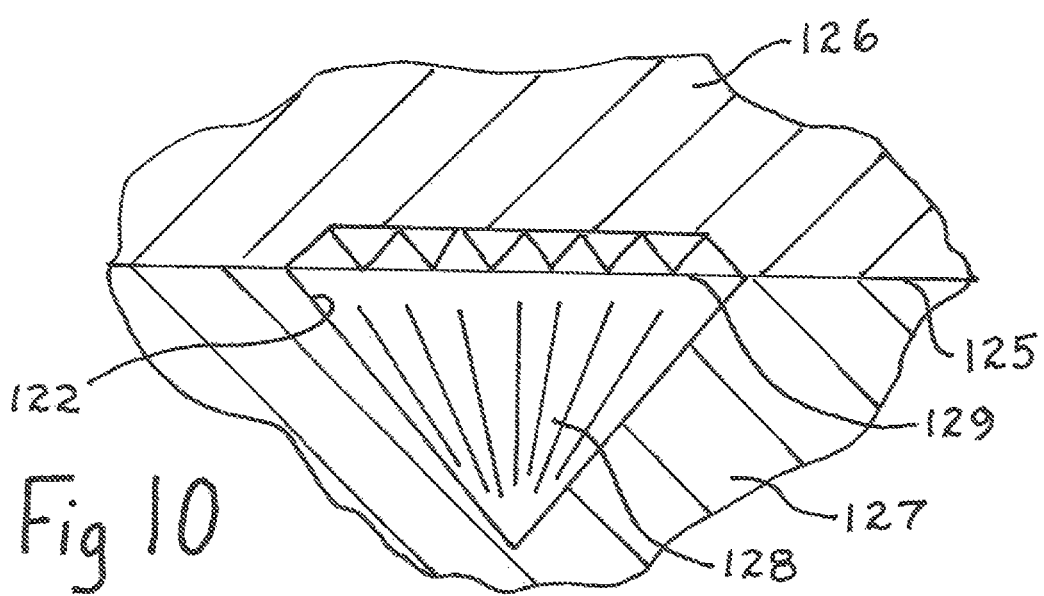
FIG. 10 sets forth a partial section view of an illustrative mold used in fabricating the present invention confectionary resembling a jewel.

FIG. 10 shows a partial section view of mold 120 to show an important aspect of the present invention. Specifically, mold body halves 126 and 127 are shown joined to form parting line 125. Mold cavity 122 is positioned with respect to parting line 125 to form edge 129 at the mold parting line. In this manner, the resulting molded confectionary 128 masks the effect of parting line 125 as edge 129. As a result, the molded confectionary produced is not marred by the parting line effect.

Figure 11:
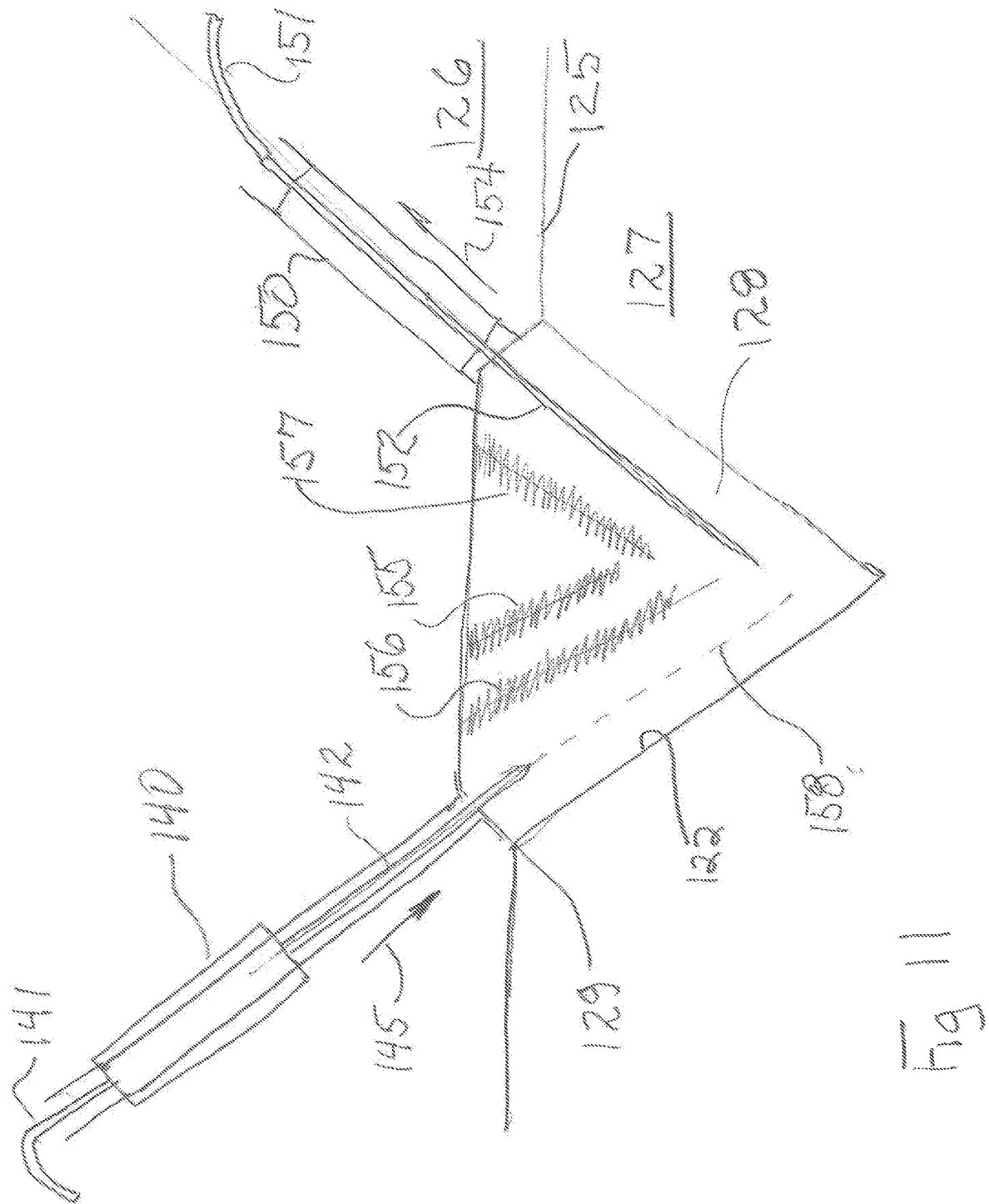
FIG. 11 sets forth an enlarged partial section view of an illustrative mold used in fabricating the present invention confectionary resembling a jewel in which an illustrative plurality of shimmer injectors are shown.

FIG. 11 shows an enlarged view of the partial section view of molded confectionary 128 within mold 120 shown above in FIG. 10 illustrating the shimmer material injection which, in accordance with an important aspect of the present invention, gives the gem confectionary a novel light-reflecting faceted appearance. Specifically, and as is mentioned above, mold body halves 126 and 127 are shown joined to form parting line 125. Mold cavity 122 is positioned with respect to parting line 125 to form edge 129 at the mold parting line. In this manner, the resulting molded confectionary 128 masks the effect of parting line 125 as edge 129. As a result, the molded confectionary produced is not marred by the parting line effect.

By way of overview and in accordance with an important aspect of the present invention, FIG. 11 illustrates the novel method by which the present invention confectionary resembling jewels is further enhanced by providing a plurality of internal reflective boundaries formed of a dispersal of edible shimmer material injected during the cooling stage of jewel 128. In further accordance with the inventive method a plurality of needle injectors are positioned within mold bodies 126 and 127 and are movable to insert elongated injection syringe needles into the molten mass of jewel confectionary 128 prior to its full cooling cycle. Each syringe injector is coupled to a supply of a slurry of edible shimmer material and the confectionary material from which confectionary jewel 128 is formed. Each injector moves into the confectionary mass and is withdrawn while injecting the mixture of edible shimmer material and molten confectionary material leaving behind a dispersed shimmer "facet" within the jewel body. Once a plurality of such facets have been simulated within the Joule body the internal reflective qualities of the jewel body closely replicate the light reflective characteristics of an actual faceted jewel.

More specifically, FIG. 11 shows confectionary jewel 128 during its cooling cycle. For purposes of illustration a pair of shimmer material injectors 140 and 150 are shown. However, it will be apparent to those skilled in the art that in a practical confectionary manufacture and enhanced the fact is provided if a greater number of shimmer material injectors are utilized. Shimmer material injector 140 includes a syringe needle 142 coupled to a supply of shimmer material and confectionary material slurry 141. Injector 140 is supported within mold half 126 by conventional fabrication (not shown). Similarly injector 150 is also shown supported within mold half 126 and includes a syringe needle 152 and a supply coupling 151 which will be understood to be coupled to a source of shimmer material and confectionary material slurry.

In operation injector 140 is shown just prior to a cycle of injection as syringe needle 142 is moved downwardly in the direction indicated by arrow 145 piercing confectionary mass 128 along axis 158. As needle 142 is moved downwardly into confectionary body 128 it assumes the position shown by injector 150 having needle 152 fully extended into confectionary body 128. Injector 150 having completed the insertion of needle 152 withdraws needle 152 outwardly in the direction indicated by arrow 154 and in Jack's a quantity of the shimmer material and confectionary material slurry as it moves out to fill the void left by the retracting needle. This cycle is repeated to produce a plurality of shimmer lines such as lines 155, 156 and 157.

In accordance with the preferred fabrication of the present invention the shimmer injecting apparatus should be able to inject an arrangement and amount of edible shimmer material to create detailed crown, table, girdle and pavilion facets during the fabrication process utilizing quick piercing motions to avoid making unnecessary streaks or clouding of the base candy material.

In the preferred method the process is initiated by weighing or dosing followed by the dissolving process to provide a uniform next of the base ingredients (hot water, isomalt etc.). The batch cooking process should be semi-continuous, open heated and double jacketed kettle cooking at 300-320° F. The target cooking temperature is preferably 330° F. removing heat at approximately 333° F. The addition of additives may be achieved easily by way of an in-line mixing grew type of apparatus while the melt material is at 230° F.

It will be apparent to those skilled in the art that while the example shown in FIGS. 9 and 10 is a round cut diamond, the invention applies to virtually any gem type or cut. Similarly, the additive may be virtually any color, tint or combination of additives. Special effects may also be used to provide various colored elements within the molded confectionary What has been shown is a novel confectionary resembling jewels which in turn utilizes a plurality of breath enhancing formula to provide an improved breath and oral hygiene for the user. The inventive confectionary are shaped and colored to resemble well known jewels and typically provide an enhanced additional flavor which is coordinated to the color with which the confectionary are tinted. A dispensing wand utilized in placing the confectionary at desired locations is also set forth.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. A confectionary comprising:
    a jewel-shaped candy having a candy body defining a shape resembling a jewel and having a color tint and flavor, said candy body having an outer surface defining a plurality of outer facets;
    a plurality of dispersed shimmer facets formed at mutually converging angles within said candy body
    a breath-enhancing substance added to said jewel-shaped candy; and
    a package receiving and displaying said jewel-shaped candy,
    said jewel-shaped candy formulated to include a Xylitol base ingredient, an odor-neutralizing ingredient, a fruit sugar, a saliva production enhancing ingredient, and a flavor ingredient.

2. The confectionary as set forth in claim 1 wherein said plurality of dispersed shimmer facets each comprise a closed-end elongated piercing void filled with a quantity of shimmer material.

3. A confectionary comprising:
    a jewel-shaped candy having a candy body defining a shape resembling a jewel and having a transparent color tint and flavor;
    said candy body defining an outer surface formed to include a plurality of outer facets and a plurality of internal reflective boundaries each formed of a dispersal of shimmer matieral
    said internal reflective boundaries converging at common angles.

4. A confectionary comprising:
    a jewel-shaped candy body having an outer surface, said candy body defining a shape resembling a jewel and having a transparent color tint and flavor;
    a plurality of outer facets formed on said outer surface;
    a plurality of elongated voids in said candy body each formed by piercing said candy body; and
    a plurality of internal reflective boundaries within said candy body each of said internal reflective boundaries including a dispersal of edible shimmer material into one of said elongated voids,
    said internal reflective boundaries converging within said candy body.

* * * * *